(12) United States Patent
Weston-Davies

(10) Patent No.: US 9,522,171 B2
(45) Date of Patent: Dec. 20, 2016

(54) EV576 FOR USE IN THE TREATMENT OF VIRAL INFECTIONS OF THE RESPIRATORY TRACT

(71) Applicant: Volution Immuno Pharmaceuticals SA, Geneva (CH)

(72) Inventor: Wynne Weston-Davies, Cheltenham (GB)

(73) Assignee: Volution Immuno Pharmaceuticals SA, Geneva (CH)

( * ) Notice: Subject to any disclaimer, the term of this patent is extended or adjusted under 35 U.S.C. 154(b) by 0 days.

(21) Appl. No.: 14/588,616

(22) Filed: Jan. 2, 2015

(65) Prior Publication Data
US 2015/0196619 A1 Jul. 16, 2015

Related U.S. Application Data

(63) Continuation of application No. 13/521,011, filed as application No. PCT/GB2011/000022 on Jan. 10, 2011, now abandoned.

(30) Foreign Application Priority Data

Jan. 8, 2010 (GB) .................................. 1000318.4
Mar. 25, 2010 (GB) .................................. 1005071.4

(51) Int. Cl.
A61K 38/17 (2006.01)
A61K 38/16 (2006.01)

(52) U.S. Cl.
CPC ........... *A61K 38/1767* (2013.01); *A61K 38/16* (2013.01)

(58) Field of Classification Search
None
See application file for complete search history.

(56) References Cited

U.S. PATENT DOCUMENTS

| | | |
|---|---|---|
| 7,884,066 B2 | 2/2011 | Ting |
| 7,884,069 B2 | 2/2011 | Schaebitz et al. |
| 2007/0141573 A1* | 6/2007 | Nunn ............... C07K 14/43527 435/6.14 |
| 2010/0105611 A1 | 4/2010 | Hamer |
| 2011/0059885 A1 | 3/2011 | Lea et al. |

FOREIGN PATENT DOCUMENTS

| | | |
|---|---|---|
| WO | WO-93/17099 A1 | 9/1993 |
| WO | WO-2007/028968 A1 | 3/2007 |
| WO | WO-2007/117241 A1 | 10/2007 |
| WO | WO-2008/029167 A1 | 3/2008 |
| WO | WO-2008/029169 A2 | 3/2008 |
| WO | WO-2009/098454 A2 | 8/2009 |

OTHER PUBLICATIONS

Bauer et al. Clinical Infectious Diseases 2006; 43:748-56.*
Asghar et al., Inhibition of Complement by a Series of Substituted 2-Aryl-1, 3-Indandiones: Interaction with the Fifth Component of Complement, Molecular Immunology, 23:459-465 (1986).
Astigarraga et al., Host immune response evasion strategies in Ornithodoros erraticus and O. moubata and their relationship to the development of an antiargasid vaccine, Parasite Immunology, 19:401-410 (1997).
Bao et al., Transgenic Expression of a Soluble Complement Inhibitor Protects Against Renal Disease and Promotes Survival in MRUlpr Mice, Journal of Immunology, 168:3601-3607 (2002).
Baranda et al., Purification, N-terminal sequencing and diagnostic value of the major antigens of Ornithodoros erraticus and O. moubata, Veterinary Parasitology, 87:193-206 (2000).
Bedford, J.M. and Witkin, S.S., Influence of complement depletion on sperm function in the female rabbit, Journal of Reproductive Fertility, 69:523-528 (1983).
Biesecker, G. et al., Derivation of,RNA aptamer inhibitors of human complement C5, Immunopharmacology. 42:219-230 (1999).
Bumpers, H.L. and Baum, J., The Effect of a Novel C5 Inhibitor (K-76 COONa) on Tumor Cell Chemotaxis, Journal of Laboratory and Clinical Medicine, 102(3):421-427 (1983).
Cicchetti et al., Combined Inhibition of Apoptosis and Complement Improves Neural Graft Survival of Embryonic Rat and Porcine Mesencephalon in the Rat Brain, Experimental Neurology. 177:376-384 (2002).
Diamond et al., Human CD59 expressed in transgenic mouse hearts inhibits the activation of complement, 3:305-312 (1995).
Ember et al., Characterization of Complement Anaphylatoxins and Their Biological Responses. In: The Human Complement System in Health and Disease, Volanakis, J.E., Frank, M.M. (Eds.), Marcel Dekker, New York, 241-284, (1998).
Evans et al., In Vitro and In Vivo Inhibition of Complement Activity by a Single-chain Fv Fragment Recognizing human C5, Molecular Immunology, 32(16): 1183-1195 (1995).
Fecke et al., Protection of hDAF-transgenic porcine endothelial cells against activation by human complement: role of the membrane attack complex, Xenotransplantation, 9:97-105 (2002).
Feuillard et al., Comparative study of in vitro inhibition of activation of the classical and alternative pathways of human complement by the magnesium and sodium salts of the anti-inflammatory peptide N-acetyl-aspartyl-glutamic acid (NAAGA), Agent and Actions, 32:343-346 (1991).
Fiorante et al., Low molecular weight dextran sulfate prevents complement activation and delays hyperacute rejection in pig-to-human xenotransplantation models, Xenotransplantation. 8:24-35 (2001).
Fitch et al., Pharmacology and Biological Efficacy of a Recombinant, Humanized, Single-Chain Antibody C5 Complement Inhibitor in Patients Undergoing Coronary Artery Bypass Graft Surgery With Cardiopulmonary Bypass, Circulation, 100:2499-2506 (1999).
Frei et al., Generation of a monoclonal antibody to mouse C5 application in an ELISA assay for detection of anti-05 antibodies, Molecular Celleular Probes, 1:141-149 (1987).

(Continued)

*Primary Examiner* — Amber D Steele
*Assistant Examiner* — Schuyler Milton
(74) *Attorney, Agent, or Firm* — McNeill Baur PLLC

(57) ABSTRACT

The present invention relates to methods of treating and preventing the inflammatory effects of viral infection of the upper and lower respiratory tracts, including infection by SARS coronovirus (SARS), pandemic Influenza A H5N1 (avian influenza) and pandemic influenza A H1N1 (swine 'flu).

28 Claims, 12 Drawing Sheets

(56) References Cited

OTHER PUBLICATIONS

Figure 1:
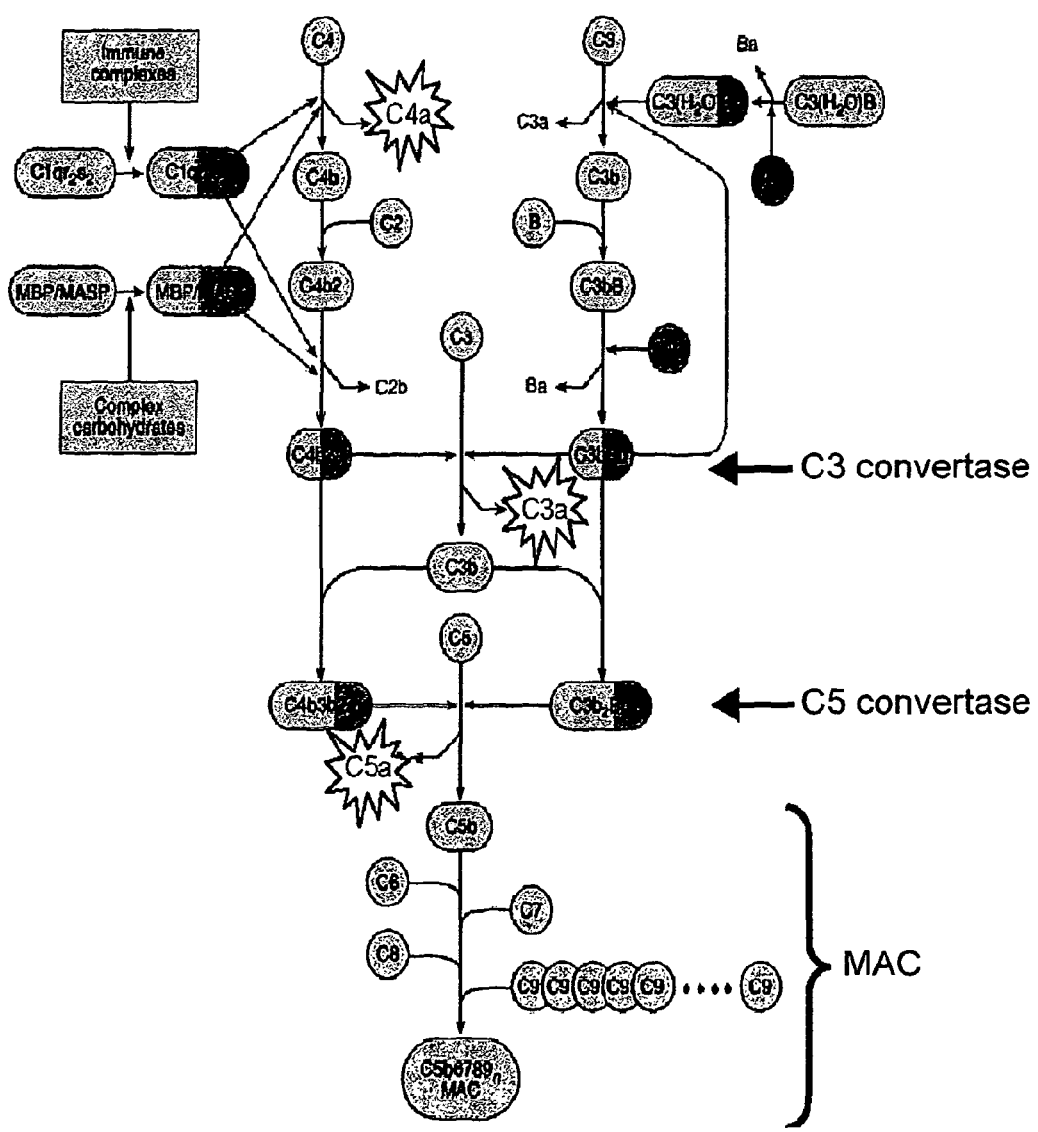
Figure 3:
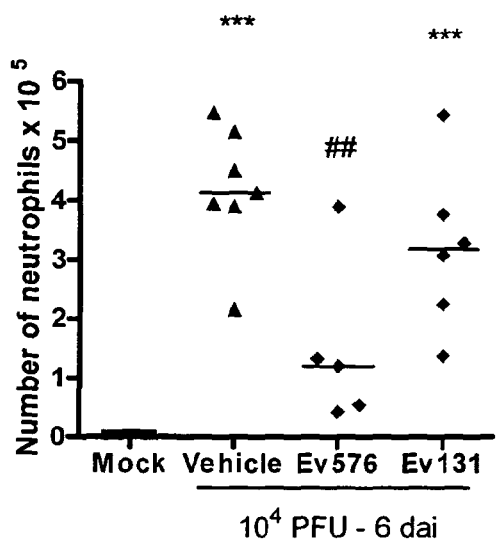
Figure 4:
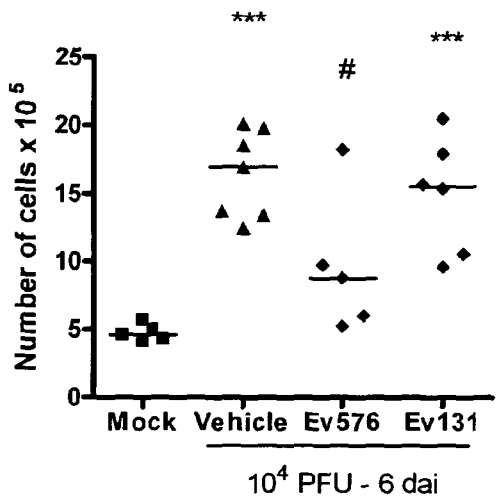
Figure 5:
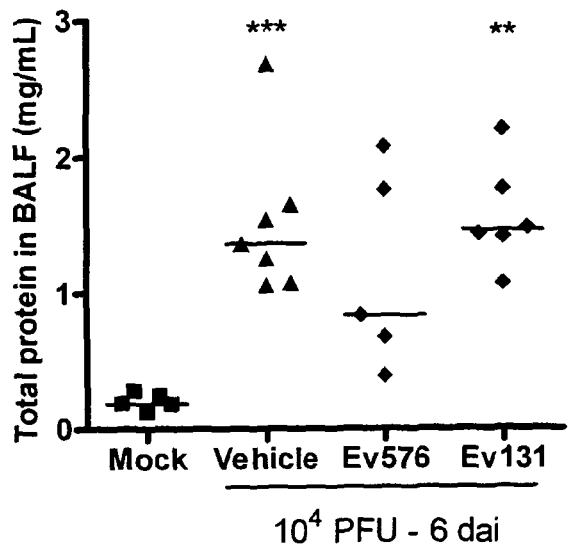
Figure 6:
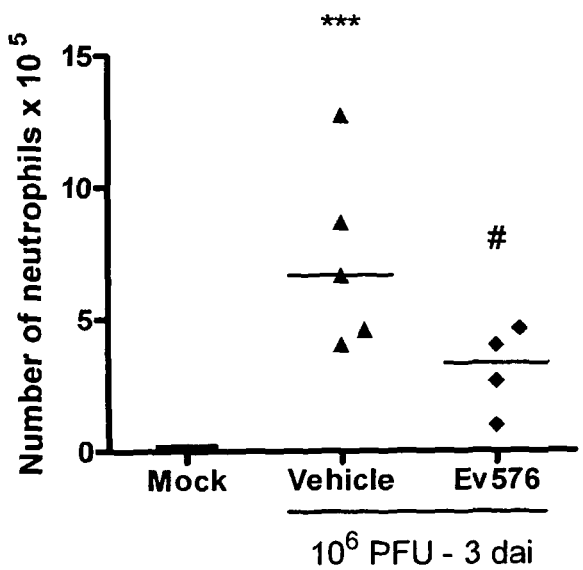
Figure 7:
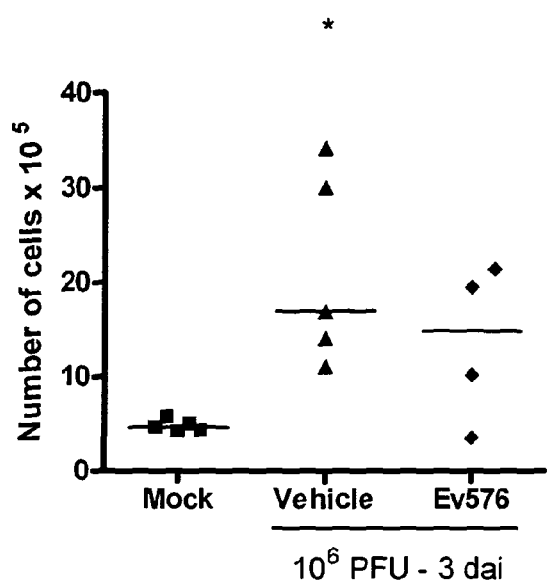
Figure 8:
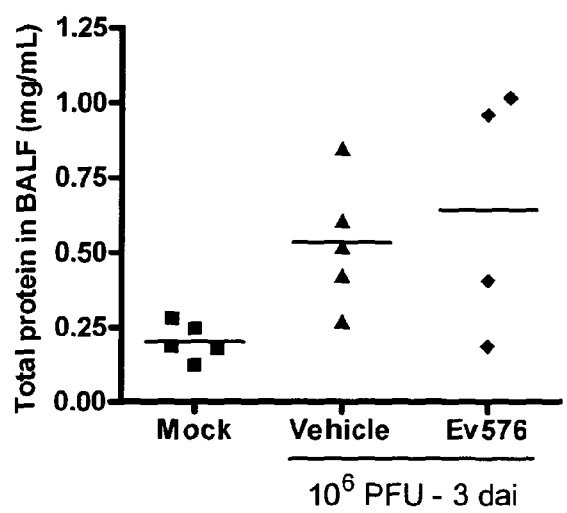
Figure 9:
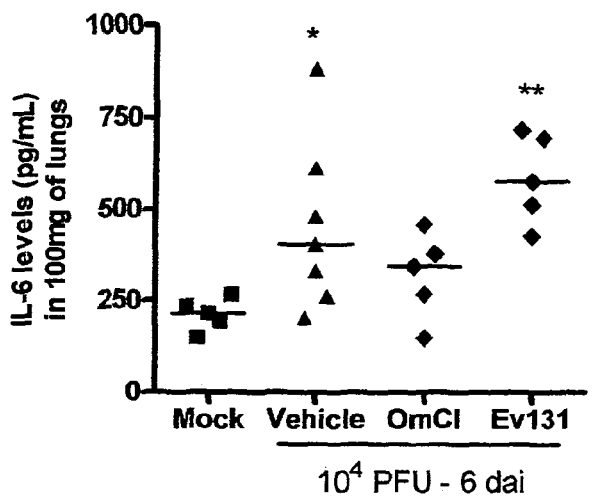
Figure 10:
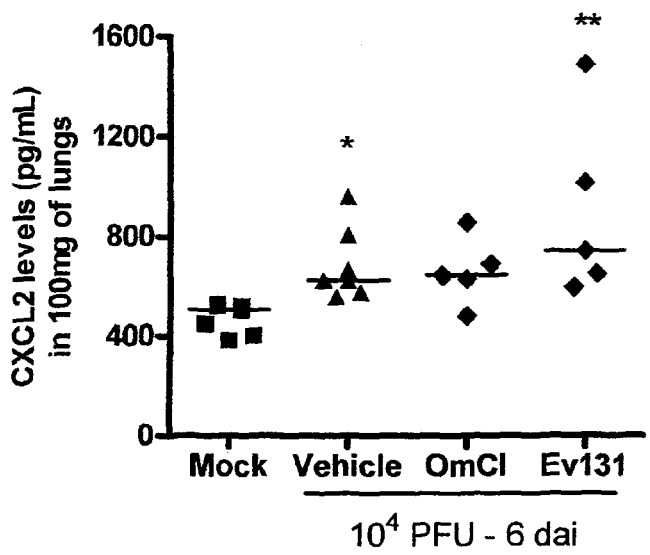
Figure 11:
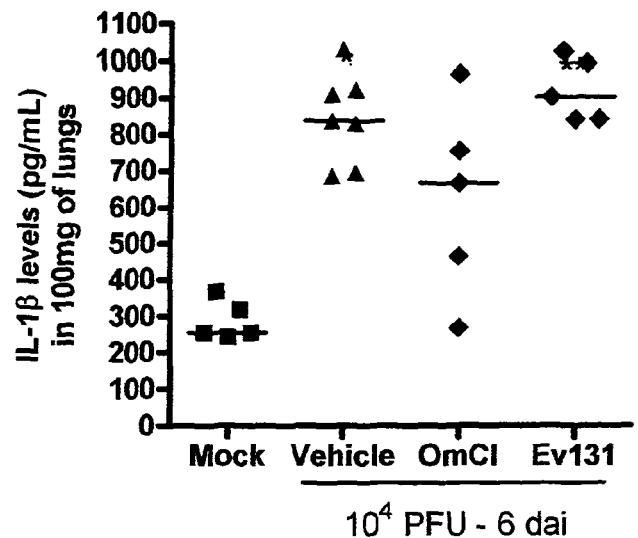
Figure 12:
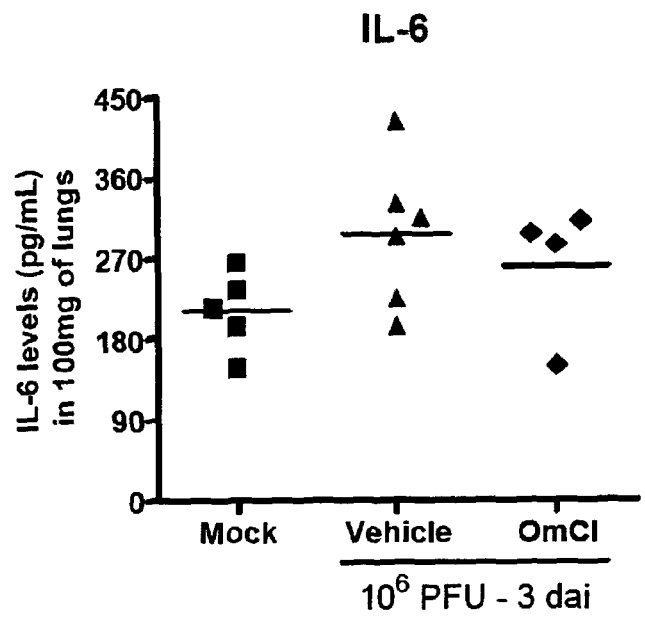
Figure 13:
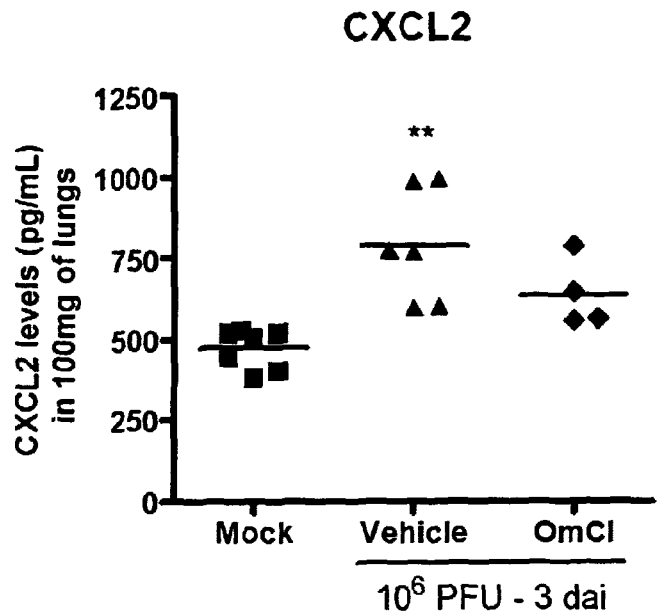
Figure 14:
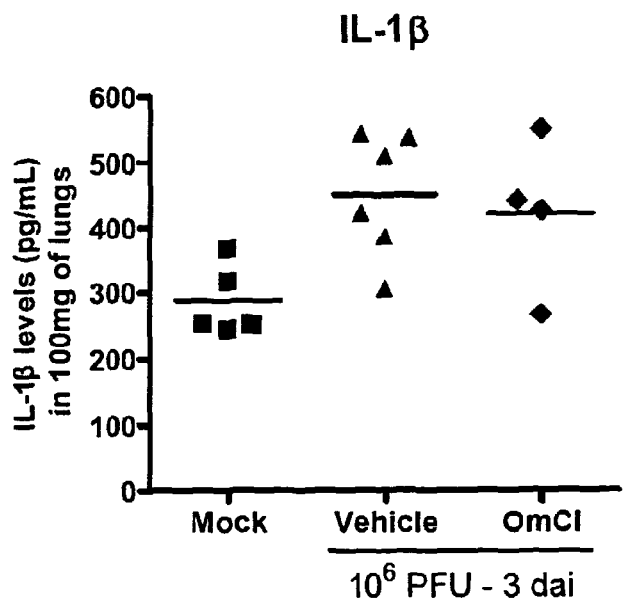
Figure 15:
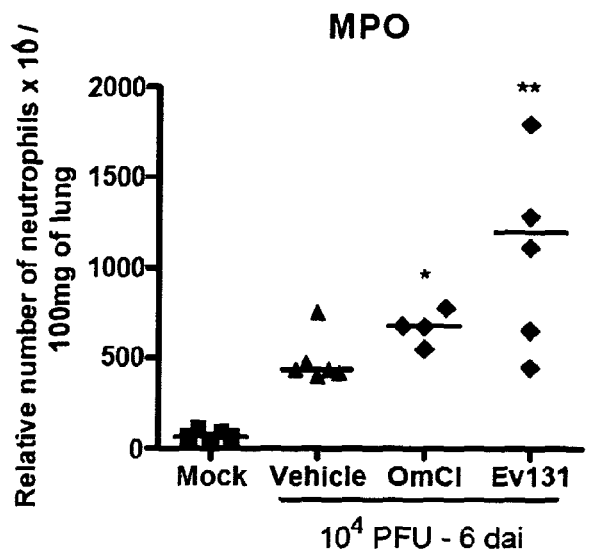
Figure 16:
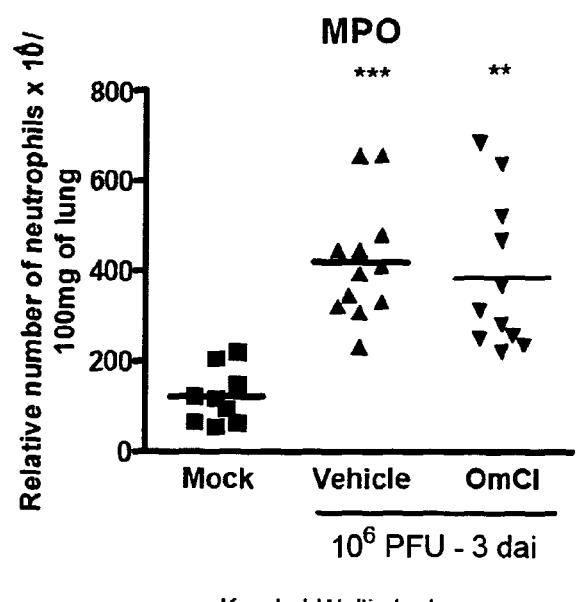
Figure 17:
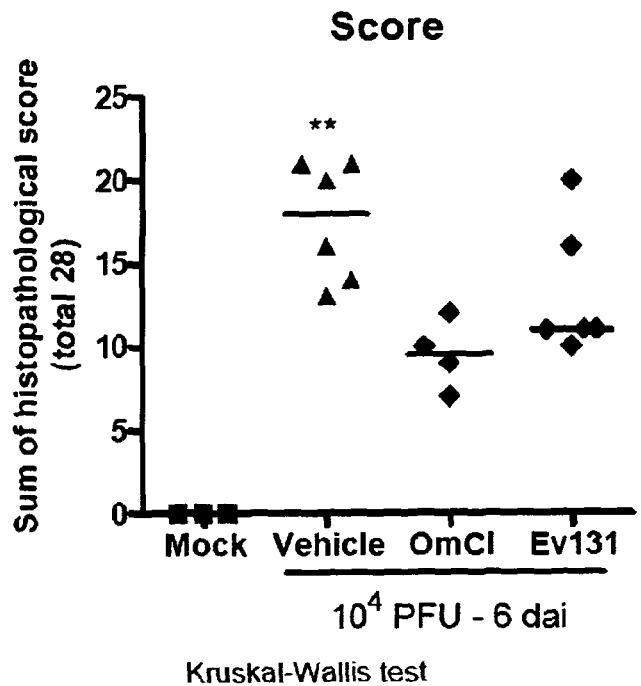

Giclas, P.C., Classical pathway evaluation and alternative pathway evaluation (sections 13.1. and 13.2), In: Current Protocols in Immunology, Editors: J.E. Coligan, A.M. Kruisbeek, D.H. Marguiles, E.M. Shevach and W. Strober, vol. 3 (1994).
Gonzalez et al., Complement and natural antibody are required in the long-term memory response to influenza virus, Vaccine, 26S: 186-193 (2008).
Hebell et al., Suppression of the Immune Response by a Soluble Complement Receptor of B Lymphocytes, 254:102-105 (1991).
Homeister et al., Effects of Complement Activation in the Isolated Heart, Circulation Research, 71:303-319 (1992).
International Search Report for PCT/GB2011/00022, 4 pages (Apr. 20, 2011).
Jarvis et al., IgM rheumatoid factor and the inhibition of covalent binding of C4b to IgG in immune complexes, Clinical Experimental Rheumatology, 11:135-141 (1993).
Keller et al., Cloning of the cDNA and Expression of Moubatin, an Inhibitor of Platelet Aggregation, Journal of Biological Chemistry, 268:5450-5456 (1993).
Konttinen et al., Complement in acute and chronic arthritides: assessment of C3c, C9 and protectin (CD59) in synovial membrane, Ann. Rheum. Dis., 55:888-894 (1996).
Kopf, M. et al., Complement component C3 promotes T-cell priming and lung migration to control acute influenza virus infection, Nature Medicine, 8:373-378 (2002).
Kroshus et al., A recombinant soluble chimeric complement inhibitor composed of human CD46 and CD55 reduces acute cardiac tissue injury in models of pig-to-human heart transplantation, Transplantation, 69:2282-2289 (2000).
Köhl, J., Anaphylatoxins and infectious and non-infectious inflammatory diseases, Molecular Immunology, 38;175-187 (2001).
Link et al., Selection of phage-displayed anti-guinea pig C5 or C5a antibodies and their application in xenotransplantation, Molecular Immunology, 36:1235-1247 (1999).
Mans et al., Identification of putative proteins involved in granule biogenesis of tick salivary glands, Electrophoresis, 22:1739-1746 (2001).
Mans et al., Pathogenic mechanisms of sand tampan toxicoses induced by the tick, *Ornithodoros savignyi*, Toxicon, 40:1007-1016 (2002).
McKenzie et al., Regulation of Complement Activity by Vaccinia Virus Complement-Control Protein, Journal of Infectious Diseases, 166:1245-1250 (1992).
Miletic, V.D. and Popovic, O., Complement activation in stored platelet concentrates, Transfusion, 33:150-154 (1993).
Mulligan, M. et al., Endothelial Targeting and Enhanced Anti-inflammatory Effects of Complement Inhibitors Possessing Sialyl Lewis' Moieties, Journal of Immunology, 162:4952-4959 (1999).
Paesen et al., Tick Histamine-Binding Proteins: Isolation, Cloning, and Three-Dimensional Structure, Molecular Cell, 3:661-671 (1999).
Paesen et al., Tick histamine-binding proteins: lipocalins with a second binding cavity, Biochimica et Biophysica Acta, 1482:92-101 (2000).
Pratt et al., Effects of Complement Inhibition with Soluble Complement Receptor-1 on Vascular Injury and Inflammation during Renal Allograft Rejection in the Rat, American Journal of Pathology, 149:2055-2066 (1996).
Rehrig et al., Complement Inhibitor, Complement Receptor 1-Related Gene/Protein y-Ig-Attenuates Intestinal Damage After the Onset of Mesenteric Ischemia/Reperfusion Injury in Mice, Journal of Immunology, 167:5921-5927 (2001).
Ribeiro, Ixodes dammini: Salivary Anti-complement Activity, Experimental Parasitology, 64:347-353 (1987).
Rinder et al., Blockade of C5a and C5b-9 Generation Inhibits Leukocyte and Platelet Activation during Extracorporeal Circulation, Journal of Clinical Investigation, 96: 1564-1572 (1995).
Rollins et al., Anti-C5 Single Chain Antibody Therapy Blocks Complement & Leukocyte Activation and Reduces Myocardial Tissue Damage in CPB Patients, Molecular Immunology, 35:397-397 (1998).
Rollins et al., Retroviral Vector Producer Cell Killing in Human Serum Is Mediated by Natural Antibody and Complement: Strategies for Evading the Humoral Immune Response, Human Gene Therapy. 7:619-626 (1996).
Sandoval et al., Distal Recognition Site for Classical Pathway Convertase Located in the C345C/Netrin Module of Complement Component C5, The Journal of Immunology, 165:1066-1073 (2000).
Schiller et al., Expression of a Soluble Complement Inhibitor Protects Transgenic Mice from Antibody-Induced Acute Renal Failure, Journal of the American Society of Nephrology, 12:71-79 (2001).
Seffernick et al, Melamine deaminase and atrazine chlorohydrolase: 98 percent identical but functionally different, J. Bacteriology, 183:2405-2410 (2001).
Smith et al., Aspirin selectively inhibits prostaglandin production in human platelets, Nature: New Biology, 231:235-237 (1971).
Smith et al., Membrane-targeted complement inhibitors, Molecular Immunology, 38:249-255 (2001).
Sodetz, J. and Plumb, M. et al., Complement: Terminal Pathway, Encyclopedia of Life Sciences, p. 1-6 (2001).
Solomon et al., Transmission of antibody-induced arthritis is independent of complement component 4(C4) and the complement receptors 1 and 2 (CD21/35), European Journal of Immunology, 32:644-651 (2002).
Tanaka et al., Effect of Anti-complement Agent K76 COOH On Hamster-To-Rat and Guinea Pig-to-Rat Heart Xenotransplantation, Transplantation, 62:681-688 (1996).
Thomas et al., Sulfonated Dextran Inhibits Complement Activation and Complement Dependent Cytotoxicity in an in vitro Model of Hyperacute Xenograft Rejection, Molecular Immunology, 33:643-648 (1996).
Vakeva et al., Myocardial Infarction and Apoptosis After Myocardial Ischemia and Reperfusion-Role of the Terminal Complement Components and Inhibition by Anti-05 Therapy, Circulation, 97:2259-2267 (1998).
Valenzuela et al., Purification, Cloning, and Expression of a Novel Salivary Anti-complement Protein from the Tick, *Ixodes scapularis*, Journal of Biology Chemistry, 275:18717-18723 (2000).
Wang et al., Amelioration of lupus-like autoimmune disease in NZB/WF, mice after treatment with a blocking monoclonal antibody specific for complement component C5, Proceedings of the National Academy of Science USA, 93:8563-8568 (1996).
Wang et al., Anti-C5 monoclonal antibody therapy prevents collagen-induced arthritis and ameliorates established disease, Proceedings of the National Academy of Science USA, 92:8955-8959 (1995).
Ward et al., Use of Animal Models to Define Complement Functions, In: Contemporary Immunology: Therapeutic Interventions in the Complement System, Lambris, J.D., Holers, V.M. (Eds.), Humana Press, Totowa, NJ, 237-253 (2000).
Weisman et al., Soluble Human Complement Receptor Type 1: In vivo Inhibitor of Complement Suppressing Post-Ischemic Myocardial Inflammation and Necrosis, Science, 249:146-151 (1990).
Wells, James A., Additivity of Mutational Effects in Proteins, Biochemistry 29(37):8509-8517 (1990).
White, Jr. et al., Suppression of mouse complement activity by contaminants of technical grade pentachlorophenol, Agents and Actions, 16:385-392 (1985).
Written Opinion for PCT/GB2011/00022, 7 pages (Apr. 20, 2011).
Wyss-Coray et al., Prominent neurodegeneration and increased plaque formation in complement-inhibited Alzheimer's mice, Proceedings of the National Academy of Science USA, 99:10837-10842 (2002).
Zhang et al., Targeting of Functional Antibody-Decay-accelerating Factor Fusion Proteins to a Cell Surface, Journal of Biology Chemistry, 276:27290-27295 (2001).

* cited by examiner

FIG. 2

```
ATGCTGGTTTTGGTGACCCTGATTTTCTCCTTTTCTGCAACATCGCATATGCTGACAGC    60
 M  L  V  V  L  V  T  L  I  F  S  F  S  A  N  I  A  Y  A  D  S    20
GAAAGCGACTGCACTGGAAGCGAACCTGTTGACGCCTTCCAAGCTTTCAGTGAGGCAAA   120
 E  S  D  C  T  G  S  E  P  V  D  A  F  Q  A  F  S  E  G  K    40
GAGGCATATGTCCTGGTGAGGTCCACGGATCCCAAAGCGAGGGACTGCTTGAAAGGAGAA   180
 E  A  Y  V  L  V  R  S  T  D  P  K  A  R  D  C  L  K  G  E    60
CCAGCCGGAGAAAAGCAGGACAACACGTTGCCGGTGATGATGACGTTTAAGAATGGCACA   240
 P  A  G  E  K  Q  D  N  T  L  P  V  M  M  T  F  K  N  G  T    80
GACTGGGCTTCAACCGATTGGACGTTTACTTTGGACGGCGCAAAGGTAACGGCAACCCTT   300
 D  W  A  S  T  D  W  T  F  T  L  D  G  A  K  V  T  A  T  L   100
GGTAACCTAACCCAAAATAGGAAGTGGTCTACGACTCGCAAAGTCATCACTGCCACGTT   360
 G  N  L  T  Q  N  R  E  V  V  Y  D  S  Q  S  H  H  C  H  V   120
GACAAGGTCGAGAAGGAAGTTCCAGATTATGAGATGTGGATGCTCGATGCGGGAGGCTT   420
 D  K  V  E  K  E  V  P  D  Y  E  M  M  L  D  A  G  G  L   140
GAAGTGGAAGTCGAGTGCTGCCGTCAAAGCTTGAAGAGTTGGCGTCTGCCAGGAACCAA   480
 E  V  E  V  E  C  C  R  Q  K  L  E  E  L  A  S  G  R  N  Q   160
ATGTATCCCCATCTCAAGGACTGCTAG                                  507
 M  Y  P  H  L  K  D  C  *                                    168
```

Kruskal-Wallis test

One-way ANOVA

Kruskal-Wallis test

Kruskal-Wallis test

EV576 FOR USE IN THE TREATMENT OF VIRAL INFECTIONS OF THE RESPIRATORY TRACT

CROSS REFERENCE TO RELATED APPLICATIONS

This application is a continuation of U.S. application Ser. No. 13/521,011, filed on Jul. 6, 2012, which is a National Stage Application of PCT Application No. PCT/GB2011/000022, filed Jan. 10, 2011, which in turn, claims priority from Great Britain application Serial No. 1000318.4, filed Jan. 8, 2010, and Great Britain application Serial No. 1005071.4, filed Mar. 25, 2010. The entire disclosure of each of the above-referenced applications is incorporated herein by reference in its entirety.

FIELD OF THE INVENTION

The present invention relates to methods of treating and preventing the inflammatory effects of viral infection of the upper and lower respiratory tracts, including infection by SARS coronovirus (SARS), pandemic Influenza A H5N1 (avian influenza) and influenza A H1N1 (swine 'flu).

All documents mentioned in the text and listed at the end of this description are incorporated herein by reference.

BACKGROUND TO THE INVENTION

The mortality associated with SARS and pandemic influenza is linked to rapidly progressive respiratory failure causing acute lung injury (ALI) or acute respiratory distress syndrome (ARDS). In some cases, multi-organ failure is also a feature. In the case of pandemic H5N1 influenza, the mortality due to respiratory and multi-organ failure is around 60%. The primary lung pathology of fatal H1N1 influenza has recently been described and is characterised by necrotising alveolitis and dense neutrophil infiltration [1].

Originally, it was assumed that respiratory failure associated with SARS and pandemic influenza was due to rapid viral replication leading to cytolytic destruction of target cells of the respiratory tract, such as alveolar epithelial cells, or to escape of the virus to tissues and organs remote from the respiratory system, such as the central nervous system. Recent evidence has shown, however, that the development of respiratory failure is not, in fact, associated with high viral titres. Investigators have instead found that respiratory failure is associated with significant elevation of pro-inflammatory cytokines such as TFNa and IFNβ. This has led experts to propose that the pathogenesis of these complications is inappropriate stimulation of the innate immune system triggering a so-called 'cytokine storm' [2, 3].

Current treatments for respiratory failure involve increasing the patient's oxygen levels using an oxygen mask, mechanical oxygenation using a ventilator or, in the most severe case, extracorporeal membrane oxygenation (ECMO) which involves circulating the patient's blood outside the body and adding oxygen to it artificially There is a great need for agents that improve upon the currently available treatments for the respiratory failure caused by the inflammatory effects of viral infection of the respiratory tract.

SUMMARY OF THE INVENTION

Accordingly, the invention provides a method of treating or preventing the inflammatory effects of viral infection of the respiratory tract comprising administering to a subject in need thereof a therapeutically or prophylactically effective amount of an agent that inhibits the classical complement pathway, the alternative complement pathway and the lectin complement pathway.

The invention also provides a therapeutically or prophylactically effective amount of an agent that inhibits the classical complement pathway, the alternative complement pathway and the lectin complement pathway for treating or preventing the inflammatory effects of viral infection of the respiratory tract.

The complement system is an essential part of the body's natural defence mechanism against foreign invasion and is also involved in the inflammatory process. More than 30 proteins in serum and at the cell surface are involved in complement system function and regulation. Recently it has become apparent that, as well as the ~35 known components of the complement system which may be associated with both beneficial and pathological processes, the complement system itself interacts with at least 85 biological pathways with functions as diverse as angiogenesis, platelet activation, glucose metabolism and spermatogenesis The complement system is activated by the presence of foreign antigens. Three activation pathways exist: (1) the classical pathway which is activated by IgM and IgG complexes or by recognition of carbohydrates; (2) the alternative pathway which is activated by non-self surfaces (lacking specific regulatory molecules) and by bacterial endotoxins; and (3) the lectin pathway which is activated by binding of manna-binding lectin (MBL) to mannose residues on the surface of a pathogen. The three pathways comprise parallel cascades of events that result in the production of complement activation through the formation of similar C3 and C5 convertases on cell surfaces resulting in the release of acute mediators of inflammation (C3a and C5a) and formation of the membrane attack complex (MAC). The parallel cascades involved in the classical and alternative pathways are shown in FIG. 1.

The complement system is recognised as being an early activator of innate immune responses initiating many inflammatory cascades. However it has not previously been implicated as being a cause of the respiratory complications of viral infection of the respiratory system. Surprisingly, the data presented in the current application show for the first time that an agent that inhibits the alternative, classical and lectin complement pathways reduces the inflammatory effects of viral infection of the respiratory tract.

Reduction of the inflammatory effects of viral infection of the respiratory tract may be assessed by reduction in inflammatory cytokines and/or neutrophils in a subject suffering from such a viral infection. In one aspect of the invention, administration of the agent that inhibits the alternative, classical and lectin complement pathways may thus reduce levels of inflammatory cytokines, such as CXCL2, IL-1β, and/or IL-6, in a subject suffering from viral infection of the respiratory tract compared to an untreated subject. Administration of the agent that inhibits the alternative, classical and lectin complement pathways to a subject suffering from a viral infection of the respiratory tract may also reduce levels of neutrophils compared to an untreated subject. Cytokine levels and neutrophil levels may, for example, be assessed in bronchoalveolar lavage (BAL) fluid from the subject.

In one aspect of the invention, the agent may bind complement C5. The agent may act to prevent the cleavage of complement C5 by C5 convertase into complement C5a and complement C5b-9. The agent may act to reduce C5a levels in a subject suffering from a viral infection of the respiratory tract, for example in the BAL fluid from such a subject, compared to an untreated subject. Surprisingly, the data presented in the current application show for the first time that there is a significant increase in C5a in BAL fluid following viral infection of the respiratory tract.

The complement C5 protein, also referred to herein as C5, is cleaved by the C5 convertase enzyme, itself formed from C3a, an earlier product of the alternative pathway (FIG. 1). The products of this cleavage include an anaphylatoxin C5a and a lytic complex C5b-9 also known as membrane attack complex (MAC). C5a is a highly reactive peptide implicated in many pathological inflammatory processes including neutrophil and eosinophil chemotaxis, neutrophil activation, increased capillary permeability and inhibition of neutrophil apoptosis [4].

MAC is associated with other important pathological processes including rheumatoid arthritis [5;6], proliferative glomerulonephritis [7], idiopathic membranous nephropathy [8], proteinurea [9], demyelination after acute axonal injury [10] and is also responsible for acute graft rejection following xenotransplantation [11].

C5a has become a target of particular interest in the field of complement-associated disorders [12]. Although C5a has many well-recognised pathological associations, the effects of its depletion in humans appear to be limited. Monoclonal antibodies and small molecules that bind and inhibit C5a or C5a receptors have been developed to treat various autoimmune diseases. These molecules do not, however, prevent the release of MAC.

In contrast, the agent used in the current invention inhibits both the formation of C5a peptide and the MAC. Since C5 is a late product of the classical and alternative complement pathways, inhibition of C5 is less likely to be associated with risks of concomitant infection that exist when targeting earlier products in the cascade [13].

The ability of an agent to bind C5 may be determined by standard in vitro assays known in the art, for example by western blotting following incubation of the protein on the gel with labelled C5. Preferably, the agent according to the invention binds C5 with an $IC_{50}$ of less than 0.2 mg/ml, preferably less than 0.1 mg/ml, preferably less than 0.05 mg/ml, preferably less than 0.04 mg/ml, preferably less than 0.03 mg/ml, preferably 0.02 mg/ml, preferably less than 1 μg/ml, preferably less than 100 ng/ml, preferably less than 10 ng/ml, more preferably still, less than 1 ng/ml.

According to one embodiment of the invention, the agent that binds C5 is not an anti-05 monoclonal antibody.

The invention also provides a method of treating or preventing the inflammatory effects of viral infection of the respiratory tract comprising administering to a subject in need thereof a therapeutically or prophylactically effective amount of an agent that inhibits eicosanoid activity.

The invention also provides a therapeutically or prophylactically effective amount of an agent that inhibits eicosanoid activity for treating or preventing the inflammatory effects of viral infection of the respiratory tract.

The agent according to this aspect of the invention may inhibit leukotrine B4 (LTB4) activity. In particular, the agent according to this aspect of the invention may bind LTB4. The ability of an agent to bind LTB4 may be determined by standard in vitro assays known in the art, for example by western blotting following incubation of the protein on the gel with labelled LTB4. The agent according to the invention may bind LTB4 with an $IC_{50}$ of less than 0.2 mg/ml, preferably less than 0.1 mg/ml, preferably less than 0.05 mg/ml, preferably less than 0.04 mg/ml, preferably less than 0.03 mg/ml, preferably 0.02 mg/ml, preferably less than 1 μg/ml, preferably less than 100 ng/ml, preferably less than 10 ng/ml, more preferably still, less than 1 ng/ml In one aspect, the invention provides a method of treating or preventing the inflammatory effects of viral infection of the respiratory tract comprising administering to a subject in need thereof a therapeutically or prophylactically effective amount of an agent that:
    a) inhibits the classical complement pathway, the alternative complement pathway and the lectin complement pathway; and
    b) inhibits eicosanoid activity.

The invention also provides a therapeutically or prophylactically effective amount of an agent that inhibits:
    a) the classical complement pathway, the alternative complement pathway and the lectin complement pathway; and
    b) eicosanoid activity,
for treating or preventing the inflammatory effects of viral infection of the respiratory tract.

According to one embodiment of this aspect of the invention, the agent binds both C5 and LTB4. The agent according to this embodiment may thus act to prevent the cleavage of complement C5 by C5 convertase into complement C5a and complement C5b-9 (MAC), and also to inhibit LTB4 activity.

The methods and uses of the invention described herein may be used to treat or prevent the inflammatory effects of viral infection of the upper or lower respiratory tracts. In particular, the methods and uses of the invention described herein may be used to treat or prevent respiratory failure caused by viral infection, including acute lung injury or acute respiratory distress syndrome. The methods and uses of the invention may also be used to treat or prevent the sequelae of respiratory failure caused by viral infection, including multi-organ failure.

The inflammation may be caused by any viral infection of the upper or lower respiratory tracts. In particular, the methods and uses of the invention may treat or prevent inflammatory effects caused by infection by pandemic influenza virus, such as influenza A H5N1 (avian influenza) and influenza A H1N1 (swine 'flu). The methods and uses of the invention may also be used to treat or prevent inflammatory effects caused by infection with SARS coronavirus.

Preferably, the agent of the invention is derived from a haematophagous arthropod. The term "haematophagous arthropod" includes all arthropods that take a blood meal from a suitable host, such as insects, ticks, lice, fleas and mites. Preferably, the agent is derived from a tick, preferably from the tick *Ornithodoros moubata*.

According to one embodiment of the invention, the agent is a protein comprising amino acids 19 to 168 of the amino acid sequence in FIG. 2 or is a functional equivalent of this protein. The agent may be a protein consisting of amino acids 19 to 168 of the amino acid sequence in FIG. 2 or be a functional equivalent of this protein.

According to an alternative embodiment, the protein used according to this embodiment of the invention may comprise or consist of amino acids 1 to 168 of the amino acid sequence in FIG. 2, or be a functional equivalent thereof. The first 18 amino acids of the protein sequence given in FIG. 2 form a signal sequence which is not required for C5 binding or for LTB4 binding activity and so this may optionally be dispensed with, for example, for efficiency of recombinant protein production.

The protein having the amino acid sequence given in FIG. 2, also referred to herein as the EV576 protein, was isolated from the salivary glands of the tick *Ornithodoros moubata*. EV576 is an outlying member of the lipocalin family and is the first lipocalin family member shown to inhibit complement activation. The EV576 protein inhibits the alternative, classical and lectin complement pathways by binding C5 and preventing its cleavage by C5 convertase into Complement C5a and Complement C5b-9, thus inhibiting both the action of C5a peptide and the MAC. The EV576 protein also binds LTB4. The term "EV576 protein", as used herein, refers to the sequence given in FIG. 2 with or without the signal sequence.

The EV576 protein and the ability of this protein to inhibit complement activation has been disclosed in [14], where the EV576 protein was referred to as the "OmCI protein". The EV576 protein has also been shown to be effective in the treatment of myasthenia gravis [15], respiratory disorders [16] and peripheral nerve disorders [17]. The ability of the EV576 protein to bind eicosanoids including LTB4 and its use in the treatment of diseases mediated by a leukotriene or hydroxyeicosanoid has been suggested in [18]. None of these disclosures suggest that the EV576 protein could be useful in the treatment or prevention of viral infection and in particular in the treatment or prevention of the inflammatory effects of viral infection of the respiratory tract.

It has now been found that the EV576 protein is surprisingly effective in the treatment and prevention of the inflammatory effects of viral infection of the respiratory tract. The data presented herein demonstrate that, in a murine model of human H1N1 influenza infection of the respiratory tract, mice treated with EV576 had significantly lower levels of protein and total cells, lower levels of complement C5a, lower levels of inflammatory cytokines IL-6, IL-1β, and CXCL2, and highly significantly lower neutrophils compared with vehicle-treated mice. EV576 thus represents a potential human therapy for the treatment and prevention of the inflammatory effects of viral infection of the respiratory tract. The surprising effectiveness of EV576 in the treatment of respiratory disorders may be due to the fact that it acts by binding C5, thus inhibiting the formation of C5a and MAC, or due to its LTB4 binding activity.

According to a further embodiment of the invention, the agent may be a nucleic acid molecule encoding the EV576 protein or a functional equivalent thereof. For example, gene therapy may be employed to effect the endogenous production of the EV576 protein by the relevant cells in the subject, either in vivo or ex vivo. Another approach is the administration of "naked DNA" in which the therapeutic gene is directly injected into the bloodstream or into muscle tissue.

Preferably, such a nucleic acid molecule comprises or consists of bases 55 to 507 of the nucleotide sequence in FIG. 2. This nucleotide sequence encodes the EV576 protein in FIG. 2 without the signal sequence. The first 54 bases of the nucleotide sequence in FIG. 2 encode the signal sequence which is not required for complement inhibitory activity or LTB4 binding activity. Alternatively, the nucleic acid molecule may comprise or consist of bases 1 to 507 of the nucleic acid sequence in FIG. 2, which encodes the protein with the signal sequence.

The EV576 protein has been demonstrated to bind to C5 and prevent its cleavage by C5 convertase in rat, mouse and human serum with an $IC_{50}$ of approximately 0.02 mg/ml. Preferably, functional equivalents of the EV576 protein which retain the ability to bind C5 with an $IC_{50}$ of less than 0.2 mg/ml, preferably less than 0.1 mg/ml, preferably less than 0.05 mg/ml, preferably less than 0.02 mg/ml, preferably less than 1 μg/ml, preferably less than 100 ng/ml, preferably less than 10 ng/ml, more preferably still, less than 1 ng/ml.

The EV576 protein has also been demonstrated to bind LTB4. Functional equivalents of the EV576 protein may also retain the ability to bind LTB4 with a similar affinity as the EV576 protein.

In one respect, the term "functional equivalent" is used herein to describe homologues and fragments of the EV576 protein which: a) retain its ability to bind C5, and to prevent the cleavage of complement C5 by C5 convertase into complement C5a and complement C5b-9; and/or b) retain its ability to bind LTB4.

The term "functional equivalent" also refers to molecules that are structurally similar to the EV576 protein or that contain similar or identical tertiary structure, particularly in the environment of the active site or active sites of the EV576 protein that binds to C5 and/or LTB4, such as synthetic molecules. Amino acids in EV576 that are likely to be required for LTB4 binding are described in [18].

The term "homologue" is meant to include reference to paralogues and orthologues of the EV576 sequence that is explicitly identified in FIG. 2, including, for example, the EV576 protein sequence from other tick species, including *Rhipicephalus appendiculatus, R. sanguineus, R. bursa, A. americanum, A. cajennense, A. hebraeum, Boophilus microplus, B. annulatus, B. decoloratus, Dermacentor reticulatus, D. andersoni, D. marginatus, D. variabilis, Haemaphysalis inermis, Ha. leachii, Ha. punctata, Hyalomma anatolicum anatolicum, Hy. dromedarii, Hy. marginatum marginatum, Ixodes ricinus, I. persulcatus, I. scapularis, I. hexagonus, Argas persicus, A. reflexus, Ornithodoros erraticus, O. moubata moubata, O. m. porcinus,* and *O. savignyi*. The term "homologue" is also meant to include the equivalent EV576 protein sequence from mosquito species, including those of the *Culex, Anopheles* and *Aedes* genera, particularly *Culex quinquefasciatus, Aedes aegypti* and *Anopheles gambiae*; flea species, such as *Ctenocephalides felis* (the cat flea); horseflies; sandflies; blackflies; tsetse flies; lice; mites; leeches; and flatworms. The native EV576 protein is thought to exist in *O. moubata* in another three forms of around 18 kDa and the term "homologue" is meant to include these alternative forms of EV576.

Methods for the identification of homologues of the EV576 sequence given in FIG. 2 will be clear to those of skill in the art. For example, homologues may be identified by homology searching of sequence databases, both public and private. Conveniently, publicly available databases may be used, although private or commercially-available databases will be equally useful, particularly if they contain data not represented in the public databases. Primary databases are the sites of primary nucleotide or amino acid sequence data deposit and may be publicly or commercially available. Examples of publicly-available primary databases include the GenBank database (http://www.ncbi.nlm.nih.gov/), the EMBL database (http://www.ebi.ac.uk/), the DDBJ database (http://www.ddbj.nig.ac.jp/), the SWISS-PROT protein database (http://expasy.hcuge.ch/), PIR (http://pir.georgetown.edu/), TrEMBL (http://www.ebi.ac.uk/), the TIGR databases (see http://www.tigr.org/tdb/index.html), the NRL-3D database (http://www.nbrfa.georgetown.edu), the Protein Data Base (http://www.rcsb.org/pdb), the NRDB database (http://ncbi.nlm.nih.gov/pub/nrdb/README), the OWL database (http://www.biochem.ucl.ac.uk/bsm/dbbrowser/OWL/) and the secondary databases PROSITE (http://expasy.hcuge.ch/sprot/prosite.html), PRINTS (http://iupab.leeds.ac.uk/bmb5dp/prints.html), Profiles (http://ulrec3.unil.ch/software/PFSCAN_form.html), Pfam (http://www.sanger.ac.uk/software/pfam), Identify (http:// dna.stanford.edu/identify/) and Blocks (http://www.blocks.fhcrc.org) databases. Examples of commercially-available databases or private databases include PathoGenome (Genome Therapeutics Inc.) and PathoSeq (previously of Incyte Pharmaceuticals Inc.).

Typically, greater than 30% identity between two polypeptides (preferably, over a specified region such as the active site) is considered to be an indication of functional equivalence and thus an indication that two proteins are homologous. Preferably, proteins that are homologues have a degree of sequence identity with the EV576 protein sequence identified in FIG. 2 of greater than 60%. More preferred homologues have degrees of identity of greater than 70%, 80%, 90%, 95%, 98% or 99%, respectively with the EV576 protein sequence given in FIG. 2. Percentage identity, as referred to herein, is as determined using BLAST version 2.1.3 using the default parameters specified by the NCBI (the National Center for Biotechnology Information; http://www.ncbi.nlm.nih.gov/) [Blosum 62 matrix; gap open penalty=11 and gap extension penalty=1].

Homologues of the EV576 protein sequence given in FIG. 2 include mutants containing amino acid substitutions, insertions or deletions from the wild type sequence, for example, of 1, 2, 3, 4, 5, 7, 10 or more amino acids, provided that such mutants retain the ability to bind C5. Mutants thus include proteins containing conservative amino acid substitutions that do not affect the function or activity of the protein in an adverse manner. This term is also intended to include natural biological variants (e.g. allelic variants or geographical variations within the species from which the EV576 proteins are derived). Mutants with improved ability to bind C5 and/or LTB4 may also be designed through the systematic or directed mutation of specific residues in the protein sequence.

Fragments of the EV576 protein and of homologues of the EV576 protein are also embraced by the term "functional equivalents" providing that such fragments retain the ability to bind C5 and/or LTB4. Fragments may include, for example, polypeptides derived from the EV576 protein sequence which are less than 150 amino acids, less than 125 amino acids, less than 100 amino acids, less than 75 amino acids, less than 50 amino acids, or even 25 amino acids or less, provided that these fragments retain the ability to bind to complement C5.

Included as such fragments are not only fragments of the O. moubata EV576 protein that is explicitly identified herein in FIG. 2, but also fragments of homologues of this protein, as described above. Such fragments of homologues will typically possess greater than 60% identity with fragments of the EV576 protein sequence in FIG. 2, although more preferred fragments of homologues will display degrees of identity of greater than 70%, 80%, 90%, 95%, 98% or 99%, respectively with fragments of the EV576 protein sequence in FIG. 2. Fragments with improved may, of course, be rationally designed by the systematic mutation or fragmentation of the wild type sequence followed by appropriate activity assays. Fragments may exhibit similar or greater affinity for C5 and/or LTB4 as EV576.

A functional equivalent used according to the invention may be a fusion protein, obtained, for example, by cloning a polynucleotide encoding the EV576 protein in frame to the coding sequences for a heterologous protein sequence. The term "heterologous", when used herein, is intended to designate any polypeptide other than the EV576 protein or its functional equivalent. Example of heterologous sequences that can be comprised in the soluble fusion proteins either at N- or at C-terminus, are the following: extracellular domains of membrane-bound protein, immunoglobulin constant regions (Fc region), multimerization domains, domains of extracellular proteins, signal sequences, export sequences, or sequences allowing purification by affinity chromatography. Many of these heterologous sequences are commercially available in expression plasmids since these sequences are commonly included in the fusion proteins in order to provide additional properties without significantly impairing the specific biological activity of the protein fused to them [19]. Examples of such additional properties are a longer lasting half-life in body fluids, the extracellular localization, or an easier purification procedure as allowed by a tag such as a histidine or HA tag.

The EV576 protein and functional equivalents thereof, may be prepared in recombinant form by expression in a host cell. Such expression methods are well known to those of skill in the art and are described in detail by [20] and [21]. Recombinant forms of the EV576 protein and functional equivalents thereof are preferably unglycosylated.

The proteins and fragments of the present invention can also be prepared using conventional techniques of protein chemistry. For example, protein fragments may be prepared by chemical synthesis. Methods for the generation of fusion proteins are standard in the art and will be known to the skilled reader. For example, most general molecular biology, microbiology recombinant DNA technology and immunological techniques can be found in [20] or [22].

The subject to which the agent is administered in the method or use of the invention is preferably a mammal, preferably a human. The subject to which the agent is administered may also be suffering from a viral infection of the upper or lower respiratory tract, such as pandemic influenza virus, including influenza A H5N1 (avian influenza) and influenza A H1N1 (swine 'flu), or SARS coronavirus.

The agent is administered in a therapeutically or prophylactically effective amount. The term "therapeutically effective amount" refers to the amount of agent needed to treat or ameliorate the inflammation associated with the viral infection The term "prophylactically effective amount" used herein refers to the amount of agent needed to prevent inflammation associated with the viral invention.

Preferably, the dose of the agent is sufficient to bind as much available C5 as possible in the subject, more preferably, all available C5. The dose of the agent may alternatively be sufficient to bind as much available LTB4 as possible in the subject, more preferably, all available LTB4. In some aspects, the dose of the agent is sufficient to binds as much available C5 and LTB4 as possible, for example all available C5 and LTB4. The dose of the agent supplied is at least twice the molar dose needed to bind all available C5 and/or LTB4 in the subject. The dose of the agent supplied may be 2.5 times, 3 times or 4 times the molar dose needed to bind all available C5 and/or LTB4 in the subject. Preferably, the dose is from 0.0001 mg/kg (mass of drug compared to mass of patient) to 20 mg/kg, preferably 0.001 mg/kg to 10 mg/kg, more preferably 0.2 mg/kg to 2 mg/kg.

The frequency with which the dose needs to be administered will depend on the half-life of the agent involved. Where the agent is the EV576 protein or a functional equivalent thereof, the dose may be administered as a continuous infusion, in bolus doses or on a daily basis, twice daily basis, or every two, three, four days, five, six, seven, 10, 15 or 20 days or more.

Figure 18:
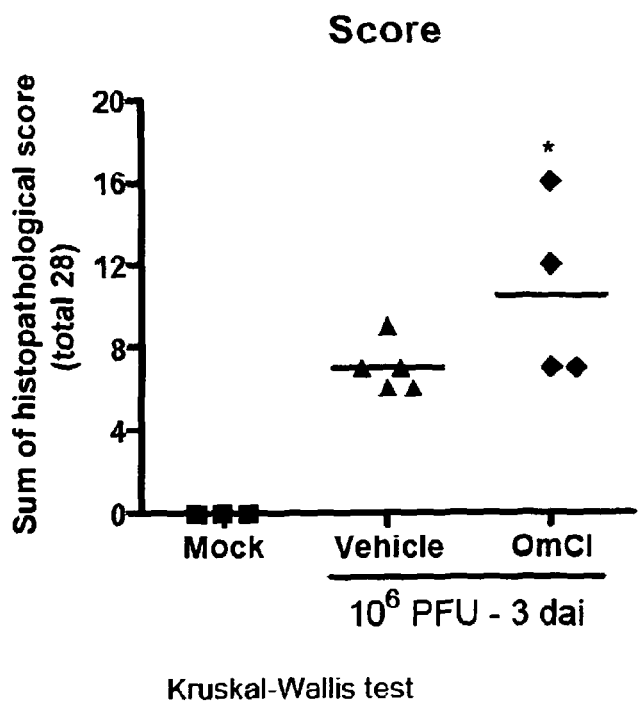

The exact dosage and the frequency of doses may also be dependent on the patient's status at the time of administration. Factors that may be taken into consideration when determining dosage include the severity of the disease state in the patient, the general health of the patient, the age, weight, gender, diet, time and frequency of administration, drug combinations, reaction sensitivities and the patient's tolerance or response to therapy. The precise amount can be determined by routine experimentation, but may ultimately lie with the judgement of the clinician.

The agent will generally be administered as part of a pharmaceutically acceptable carrier. The term "pharmaceutically acceptable carrier", as used herein, includes genes, polypeptides, antibodies, liposomes, polysaccharides, polylactic acids, polyglycolic acids and inactive virus particles or indeed any other agent provided that the carrier does not itself induce toxicity effects or cause the production of antibodies that are harmful to the individual receiving the pharmaceutical composition. Pharmaceutically acceptable carriers may additionally contain liquids such as water, saline, glycerol, ethanol or auxiliary substances such as wetting or emulsifying agents, pH buffering substances and the like. The pharmaceutical carrier employed will thus vary depending on the route of administration. Carriers may enable the pharmaceutical compositions to be formulated into tablets, pills, dragees, capsules, liquids, gels, syrups, slurries, suspensions to aid intake by the patient. A thorough discussion of pharmaceutically acceptable carriers is available in [23].

The agent may be delivered by any known route of administration. The agent may be delivered nasally, by inhalation, for example, using a metered-dose inhaler, nebuliser, dry powder inhaler, or nasal inhaler. The agent may be delivered by a parenteral route (e.g. by injection, either subcutaneously, intraperitoneally, intravenously or intramuscularly or delivered to the interstitial space of a tissue). The compositions can also be administered into a lesion. Other modes of administration include oral and pulmonary administration, suppositories, and transdermal or transcutaneous applications, needles, and hyposprays.

The agent may be administered alone or as part of a treatment regimen also involving the administration of other drugs currently used in the treatment of patients with respiratory disorders. For example, the agent may be administered in combination with the infusion of additional antiviral drugs and/or oxygen treatment.

The agent may be administered simultaneously, sequentially or separately with the other drug(s). For example, the agent may be administered before or after administration of the other drug(s).

The invention thus provides an agent that binds C5 and/or LTB4, preferably the EV576 protein or a functional equivalent thereof, for treating or preventing the inflammatory effects of viral infection of the respiratory tract in a subject, wherein said subject has been pre-treated with an anti-viral drug. Examples of anti-viral drugs that may be used in this aspect of the invention include zanamivir (Relenza) and oseltamivir (Tamiflu).

Various aspects and embodiments of the present invention will now be described in more detail by way of example. It will be appreciated that modification of detail may be made without departing from the scope of the invention.

BRIEF DESCRIPTION OF FIGURES

FIG. 1: Schematic diagram of classical and alternative pathways of complement activation. Enzymatic components, dark grey. Anaphylatoxins enclosed in starbursts.

FIG. 2: Primary sequence of EV576. Signal sequence underlined. Cysteine residues in bold type. Nucleotide and amino acid number indicated at right.

FIG. 3: Reduction in neutrophils at $10^4$ plaque forming units (PFU) following administration of EV576 to a murine model of swine flu infection compared with administration of EV131 or a vehicle in the same model.

FIG. 4: Reduction in total cells at $10^4$ plaque forming units (PFU) following administration of EV576 to a murine model of swine flu infection compared with administration of EV131 or a vehicle in the same model.

FIG. 5: Reduction in total protein at $10^4$ plaque forming units (PFU) following administration of EV576 to a murine model of swine flu infection compared with administration of EV131 or a vehicle in the same model.

FIG. 6: Reduction in neutrophils at $10^6$ plaque forming units (PFU) following administration of EV576 to a murine model of swine flu infection compared with a vehicle in the same model.

FIG. 7: Reduction in total cells at $10^6$ plaque forming units (PFU) following administration of EV576 to a murine model of swine flu infection compared with a vehicle in the same model.

FIG. 8: Reduction in total protein at $10^6$ plaque forming units (PFU) following administration of EV576 to a murine model of swine flu infection compared with a vehicle in the same model.

FIG. 9: Reduction in IL-6 level at $10^4$ plaque forming units (PFU) following administration of EV576 (OmCI) to a murine model of swine flu infection compared with administration of EV131 or a vehicle in the same model.

FIG. 10: Reduction in CXC2 level at $10^4$ plaque forming units (PFU) following administration of EV576 (OmCI) to a murine model of swine flu infection compared with administration of EV131 or a vehicle in the same model.

FIG. 11: Reduction in IL-1β at $10^4$ plaque forming units (PFU) following administration of EV576 (OmCI) to a murine model of swine flu infection compared with administration of EV131 or a vehicle in the same model.

FIG. 12: Reduction in IL-6 level at $10^6$ plaque forming units (PFU) following administration of EV576 (OmCI) to a murine model of swine flu infection compared with a vehicle in the same model.

FIG. 13: Reduction in CXC2 level at $10^6$ plaque forming units (PFU) following administration of EV576 (OmCI) to a murine model of swine flu infection compared with a vehicle in the same model.

FIG. 14: Reduction in IL-1β at $10^6$ plaque forming units (PFU) following administration of EV576 (OmCI) to a murine model of swine flu infection compared with a vehicle in the same model.

FIG. 15: Relative reduction in neutrophils per 100 mg lung tissue at $10^4$ plaque forming units (PFU) following administration of EV576 to a murine model of swine flu infection compared with administration of EV131 or a vehicle in the same model.

FIG. 16: Relative reduction in neutrophils per 100 mg lung tissue at $10^6$ plaque forming units (PFU) following administration of EV576 to a murine model of swine flu infection compared with administration of EV131 or a vehicle in the same model.

FIG. 17: Overall histopathological score at $10^4$ plaque forming units (PFU) following administration of EV576 to a murine model of swine flu infection compared with administration of EV131 or a vehicle in the same model.

FIG. 18: Overall histopathological score at $10^6$ plaque forming units (PFU) following administration of EV576 to a murine model of swine flu infection compared with a vehicle in the same model.

Figure 19:
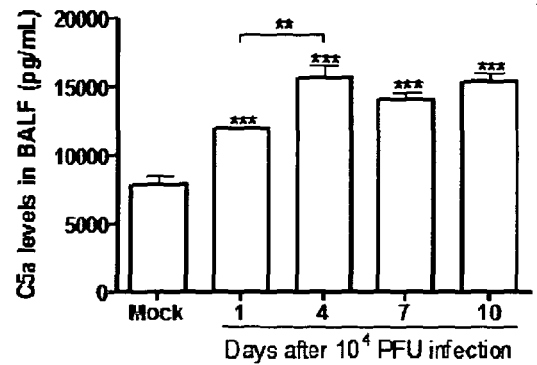

FIG. 19: C5a level in Bronchoalveolar lavage fluid (BALF) in a murine model of swine flu infection at an inoculum level of $10^4$ plaque forming units (PFU) compared with mock inoculation.

Figure 20:
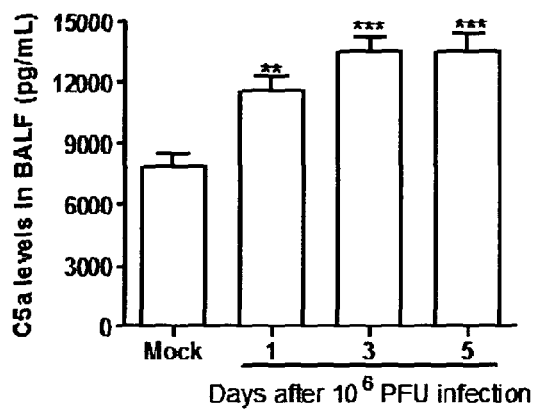

FIG. 20: C5a level in Bronchoalveolar lavage fluid (BALF) in a murine model of swine flu infection at an inoculum level of $10^6$ plaque forming units (PFU) compared with mock inoculation.

Figure 21:
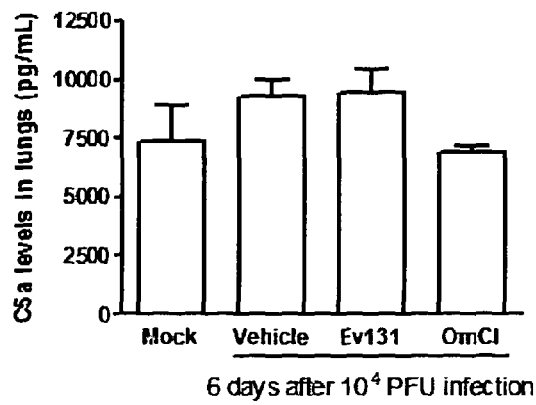

FIG. 21: Reduction in C5a level at $10^4$ plaque forming units (PFU) following administration of EV576 to a murine model of swine flu infection compared with administration of EV131 or a vehicle in the same model.

Figure 22:
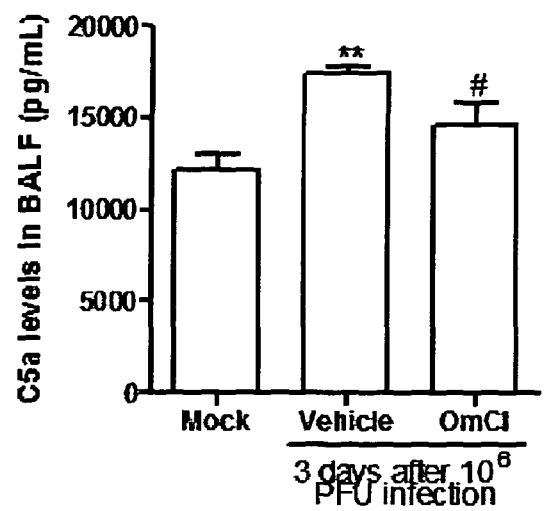

FIG. 22: Reduction in C5a level at $10^6$ plaque forming units (PFU) following administration of EV576 to a murine model of swine flu infection compared with administration of a vehicle in the same model.

Example 1

EV576 protein having the amino acid sequence shown in FIG. 2 was tested in a murine model of human H1N1 influenza infection of the respiratory tract.

Methods

BalbC mice were infected transnasally with either a sub-lethal dose ($10^4$ PFU) or a lethal dose ($10^6$ PFU) of human H1N1 virus obtained from the Institut Pasteur or sham infected using phosphate buffered saline (PBS).

Signs of lower respiratory tract infection (weight loss and respiratory congestion) developed within 4 days in low inoculum animals and more rapidly in the high inoculum group who all succumbed to the virus by the third day.

EV576 protein having the amino acid sequence shown in FIG. 2 was given by intraperitoneal injection 250 μg 30 minutes pre-infection and on Day 1, 200 μg on days 2, 3 and 4 and 170 μg on Day 5. rEV131, a similarly sized lipocalin to EV576 but which is known not to inhibit the complement system, and PBS were used as controls.

High inoculum mice received only the first two doses as they were all dead by Day 3. Bronchoalveolar lavage (BAL) was performed on Day 3 for high inoculum mice. Bronchoalveolar lavage (BAL) was performed on Day 6 for low inoculum mice, 24 hours after the last dosing and immediately prior to sacrifice. Lavage fluid was assayed for total cells, neutrophils, total protein and cytokines (IL-1β, IL-6 and CXCL2).

The results are shown in FIGS. 3-16.

All parameters were found to be highly significantly raised in vehicle treated mice compared to mock (sham) treated mice.

Results

Mice treated with EV576 had significantly lower levels of protein (FIG. 5) and total cells (FIG. 4), and highly significantly lower neutrophils (FIGS. 3 and 15) compared with vehicle treated mice at $10^4$ plaque forming units (PFU). Mice treated with EV576 also had significantly lower neutrophils at $10^6$ PFU compared to vehicle.

At $10^4$ PFU vehicle treated and rEV131 mice had highly significantly ($p<0.001$) raised total cells, neutrophils and protein compared to sham (mock) treated animals. Animals treated with EV576 had significantly less elevation of total cells ($p<0.05$) and neutrophils ($p<0.01$) than vehicle treated ones (FIGS. 3 and 4). At $10^6$ PFU only total cells ($p<0.05$) and neutrophils ($p<0.001$) were elevated compared to sham treated animals and neutrophil elevation was significantly less ($p<0.05$) in mice treated with EV576 compared to vehicle (FIGS. 6-8 and 16) but since BAL was performed on moribund animals at Day 3 instead of Day 6 it is likely that the effects of the respiratory complications of H1N1 influenza had not had time to develop fully and therefore any possible protective effects of complement inhibition were not as apparent.

In the low inoculum group levels of the inflammatory cytokines IL-1β, IL-6 and CXCL2 in BAL fluid were found to be significantly ($p<0.05$) or highly significantly ($p<0.01$) elevated in vehicle and rEV131 treated groups compared to sham (mock) treated animals (FIGS. 9-11) but, although elevated, were not significantly different in EV576 treated animals. As with the cellular results the differences were less marked in the high inoculum group (FIGS. 12-14).

The sum of all the histopathological scores of lung inflammation is show in FIGS. 17 and 18 for low and high inoculum mice respectively. The sum of the histopathological scores was calculated using scores for airway inflammation, vascular inflammation, parenchymal inflammation, neutrophilic inflammation and epithelial injury. EV576 reduced epithelial damage and inflammation in the low inoculum groups. The histamine scavenging protein EV131 was less effective.

These data demonstrate that EV576 significantly inhibits the inflammatory effects of H1N1 infection. EV576 is known to inhibit the complement system via binding of C5 and to inhibit eicosanoid activity. These data suggest that EV576 and other agents having similar C5 binding properties may be effective in reducing the lung inflammatory effects of viral infection.

Example 2

EV576 protein having the amino acid sequence shown in FIG. 2 was tested in a murine model of human H1N1 influenza infection of the respiratory tract for its effect on complement C5a level.

Methods

BalbC mice were infected and treated as described above in Example 1.

C5a levels in BALF were measured in mock inoculated animals on day, on days 1, 4, 7, and 10 in animals exposed to a sub-lethal dose ($10^4$ PFU), and on days 1, 3 and 5 in animals exposed to a lethal dose ($10^6$ PFU) of human H1N1 virus.

On day 6, C5a levels in BALF were measured in low inoculum animals that had also been treated with vehicle, EV131 or EV576. On day 3, C5a levels in BALF were measured in high inoculum animals that had also been treated with vehicle or EV576.

Results are shown in FIGS. 19 to 22.

Results

There is a significant rise in C5a in BAL fluid for up to 10 days following infection at both the high and low inoculum levels (FIGS. 19 and 20). Mice treated with EV576 had a significantly attenuated rise in C5a level. Vehicle and EV131 did not attenuate the rise in C5a level (FIGS. 21 and 22).

This is the first time that a direct role for complement has demonstrated in inflammation caused by H1N1 influenza infection. This rise in complement can be blocked using the complement inhibitor. EV576. The ability of EV576 to block complement and associated inflammation suggests that it will be effective in the treatment of H1N1 influenza infection.

Example 3

The cytokine storm and associated inflammation that follows H1N1 infection is also present following H5N1 infection. The ability of EV576 to block complement rise and associated inflammation following H1N1 infection is therefore expected to be replicated in following H5N1 infection. EV576 protein having the amino acid sequence shown in FIG. 2 can be tested in a murine model of human H5N1 influenza infection of the respiratory tract using the experimental protocol reported above and in reference 24. The effect of oseltamivir (Tamiflu) in combination with EV576 following infection with H5N1 or H1N1 influenza can also be determined.

Methods

The experimental protocol is similar to that reported in reference 24.

Pathogen-free, female, 8 week old mice with a standardised body weight of 20-23 g (e.g. FVB/J strain) are infected transnasally with human H5N1 virus or H1N1 virus obtained from the Institut Pasteur or sham infected using phosphate buffered saline (PBS).

EV576 protein having the amino acid sequence shown in FIG. 2 is given by intraperitoneal injection. Mice may also receive oseltamivir. PBS is used as a control. Four groups may be enrolled in each infection model: (1) virus+PBS, (2) virus+EV576, (3) virus+EV576+oseltamivir and (4) virus+oseltamivir. The infection and treatment schedule is shown in the table below:

Option 5: global virus distribution in lungs, by IF
Option 6: Cell countings in BALF by flow cytometry
Time points for collection of readouts will be day 2, day 3 and day 4 post infection after H5N1 or day 2, day 4, day 6, day 7, day 8 post infection after H1N1. Pre-infection values will also be determined.

REFERENCES

[1] Mastellos, D., et al., Clin Immunol, 2005. 115(3): p. 225-35
[2] Peiris J S M, Cheung C Y, Leung C Y H, Nicholls J M. Innate immune responses to influenza A H5N1:friend or foe? Trends in Immunology 2009; 30, 12: 574-584.
[3] Lee S M Y, Gardy J L, Cheung C Y et al. Systems-level comparison of host-responses elicited by avian H5N1 and seasonal H1N1 influenza viruses in primary human macrophages. PLoS One, December 2009; 4, 12: 1-11.
[4] Guo, R. F. and P. A. Ward, Annu Rev Immunol, 2005, 23: p. 821-52
[5] Neumann, E., et al., Arthritis Rheum, 2002. 46(4): p. 934-45
[6] Williams, A. S., et al., Arthritis Rheum, 2004, 50(9): p. 3035-44
[7] Quigg, R. J., Curr Dir Autoimmun, 2004.7: p. 165-80
[8] Papagianni, A. A., et al., Nephrol Dial Transplant, 2002, 17(1): p. 57-63
[9] He, C., et al., J Immunol, 2005. 174(9): p. 5750-7
[10] Mead, R. J., et al., J Immunol, 2002. 168(1): p. 458-65
[11] Nakashima, S., et al., J Immunol, 2002. 169(8): p. 4620-7
[12] Mizuno, M. and D. S. Cole, Expert Opin Investig Drugs, 2005. 14(7): p. 807-21
[13] Allegretti, M., et al., Curr Med Chem, 2005. 12(2): p. 217-36

| Experimental campaign | Group | Timepoints | | | | | |
|---|---|---|---|---|---|---|---|
| | | Day 2 pi | Day 3 pi | Day 4 pi | Day 6 pi | Day 7 pi | Day 8 pi |
| H5N1 | Virus + PBS + PBS | 5 | 5 | 5 | | | |
| | Virus + CVS + PBS | 5 | 5 | 5 | | | |
| | Virus + CVS + OSTMV | 5 | 5 | 5 | | | |
| | Virus + PBS + OSTMV | 5 | 5 | 5 | | | |
| H1N1 | Virus + PBS + PBS | 5 | | 5 | 5 | 5 | 5 |
| | Virus + CVS + PBS | 5 | | 5 | 5 | 5 | 5 |
| | Virus + CVS + OSTMV | 5 | | 5 | 5 | 5 | 5 |
| | Virus + PBS + OSTMV | 5 | | 5 | 5 | 5 | 5 |
| Total mice | | 40 | 20 | 40 | 20 | 20 | 20 |

CVS stands for coversin (EV576) and OSTMV for oseltamivir.
Numbers may be doubled.

The following signs of infection and readouts of treatment effects can be measured:
Bodyweight, daily
Group-specific % survival
Photo of each lung, dorso-ventral view, each timepoint
Lung weight, each timepoint
Lung bulk virus titer, each timepoint
Lung bulk myeloperoxidase activity, each timepoint
Option 1: histopathologic exam., each timepoint
Option 2: lung bulk neutrophil chemokines (KC and MIP-2)
Option 3: lung bulk monocyte/NK/T cells chemokines (MCP1, MIP1α)
Option 4: lung bulk cytokines (IL-6, TNFα, IFNα, IFNγ, IL-1β)

[14] WO2004/106369
[15] WO/2007/028968
[16] WO/2008/029169
[17] WO/2008/029167
[18] WO2009/098454
[19] Terpe K, Appl Microbiol Biotechnol, 60: 523-33, 2003
[20] Sambrook et al (2000)
[21] Fernandez & Hoeffler (1998)
[22] Ausubel et al. (1991)
[23] Remington's Pharmaceutical Sciences; Mack Pub. Co., N.J. 1991
[24] Garigliany et al., (2010) Emerg Infect Dis 16:595-603

The invention claimed is:

1. A method of treating viral infection comprising administering to a subject in need of treatment a therapeutically effective amount of an agent comprising amino acids 19 to 168 of SEQ. ID. NO:2 or a functional equivalent thereof, wherein the agent inhibits a) the classical complement pathway, the alternative complement pathway and the lectin complement pathway; and/or b) eicosanoid activity and one or more of:

(i) measuring a viral titer in the subject;

(ii) determining global virus distribution in lungs of the subject;

(iii) measuring a neutrophil density within the lungs of the subject;
(iv) measuring a total necrotized cell count within the lungs of the subject; and
(v) measuring a total protein level within the lungs of the subject.

2. The method of claim 1, wherein the subject is suffering from viral infection in the respiratory tract.

3. The method of claim 1, wherein the viral infection is caused by an influenza virus or a coronavirus.

4. The method of claim 3, wherein the influenza virus is an influenza A virus.

5. The method of claim 4, wherein the influenza A virus is subtype H1N1 or H5N1.

6. The method of claim 3, wherein the coronavirus is a SARS coronavirus.

7. The method of claim 1, wherein administration of the agent treats respiratory failure caused by the viral infection.

8. The method of claim 7, wherein respiratory failure caused by the viral infection includes acute lung injury or acute respiratory distress syndrome.

9. The method of claim 1, wherein administration of the agent treats sequelae of respiratory failure caused by the viral infection.

10. The method of claim 1, comprising measuring a viral titer in the subject.

11. The method of claim 10, wherein administration of the agent results in reduction of the viral titer in the subject as compared to that in the untreated subject.

12. The method of claim 11, wherein the viral titer is lung bulk virus titer.

13. The method of claim 1, comprising determining global virus distribution in lungs of the subject.

14. The method of claim 1, comprising measuring a neutrophil density within the lungs of the subject.

15. The method of claim 14, wherein administration of the agent results in reduction of the neutrophil density within the lungs of the subject as compared to that in untreated subject.

16. The method of claim 1, comprising measuring a total necrotized cell count within the lungs of the subject.

17. The method of claim 16, wherein administration of the agent results in reduction of the total necrotized cell count in the subject as compared to that in untreated subject.

18. The method of claim 1, comprising measuring a total protein level within the lungs of the subject.

19. The method of claim 18, wherein administration of the agent results in reduction of the total protein level within the lungs of the subject as compared to that within the lungs of untreated subject.

20. The method of claim 1, wherein the agent comprises amino acids 19 to 168 of SEQ. ID. NO:2.

21. The method of claim 1, wherein the agent comprises amino acids 1 to 168 of SEQ. ID. NO:2.

22. The method of claim 1, wherein the agent is encoded by a nucleic acid molecule comprising bases 55 to 507 of the nucleotide sequence in SEQ. ID. NO: 1.

23. The method of claim 1, wherein the agent is encoded by a nucleic acid molecule comprising bases 1 to 507 of the nucleotide sequence in SEQ. ID. NO: 1.

24. The method of claim 1, wherein the subject is a mammal.

25. The method of claim 24, wherein the mammal is a human.

26. The method of claim 1, wherein the therapeutically effective amount of the agent administered to the subject is from 0.0001 mg/kg to 20 mg/kg.

27. The method of claim 1, wherein the therapeutically effective amount of the agent administered to the subject is from 0.001 mg/kg to 10 mg/kg.

28. The method of claim 1, wherein the therapeutically effective amount of the agent administered to the subject is from 0.2 mg/kg to 2 mg/kg.

* * * * *

SEQUENCE LISTING

<160> NUMBER OF SEQ ID NOS: 2

<210> SEQ ID NO 1
<211> LENGTH: 507
<212> TYPE: DNA
<213> ORGANISM: Ornithodoros moubata

<400> SEQUENCE: 1

```
atgctggttt tggtgaccct gattttctcc ttttctgcga acatcgcata tgctgacagc      60
gaaagcgact gcactggaag cgaacctgtt gacgccttcc aagctttcag tgagggcaaa     120
gaggcatatg tcctggtgag gtccacggat cccaaagcga gggactgctt gaaggagaa      180 ccagccggag aaaagcagga caacacgttg ccggtgatga tgacgtttaa gaatggcaca     240
gactgggctt caaccgattg gacgtttact ttggacggcg caaaggtaac ggcaacccct     300
ggtaacctaa cccaaaatag gaagtggtc tacgactcgc aaagtcatca ctgccacgtt      360
gacaaggtcg agaaggaagt tccagattat gagatgtgga tgctcgatgc gggagggctt     420
gaagtggaag tcgagtgctg ccgtcaaaag cttgaagagt tggcgtctgg caggaaccaa     480
atgtatcccc atctcaagga ctgctag                                         507
```

<210> SEQ ID NO 2
<211> LENGTH: 168
<212> TYPE: PRT
<213> ORGANISM: Ornithodoros moubata

<400> SEQUENCE: 2

```
Met Leu Val Leu Val Thr Leu Ile Phe Ser Phe Ser Ala Asn Ile Ala
1               5                   10                  15

Tyr Ala Asp Ser Glu Ser Asp Cys Thr Gly Ser Glu Pro Val Asp Ala
            20                  25                  30

Phe Gln Ala Phe Ser Glu Gly Lys Glu Ala Tyr Val Leu Val Arg Ser
        35                  40                  45

Thr Asp Pro Lys Ala Arg Asp Cys Leu Lys Gly Glu Pro Ala Gly Glu
    50                  55                  60

Lys Gln Asp Asn Thr Leu Pro Val Met Met Thr Phe Lys Asn Gly Thr
65                  70                  75                  80

Asp Trp Ala Ser Thr Asp Trp Thr Phe Thr Leu Asp Gly Ala Lys Val
                85                  90                  95

Thr Ala Thr Leu Gly Asn Leu Thr Gln Asn Arg Glu Val Val Tyr Asp
            100                 105                 110

Ser Gln Ser His His Cys His Val Asp Lys Val Glu Lys Glu Val Pro
        115                 120                 125

Asp Tyr Glu Met Trp Met Leu Asp Ala Gly Gly Leu Glu Val Glu Val
    130                 135                 140

Glu Cys Cys Arg Gln Lys Leu Glu Glu Leu Ala Ser Gly Arg Asn Gln
145                 150                 155                 160

Met Tyr Pro His Leu Lys Asp Cys
                165
```